Jan. 1, 1974 W. H. JESSEL. JR., ET AL Plant Pat. 3,416
CHRYSANTHEMUM PLANT
Filed Oct. 22, 1971
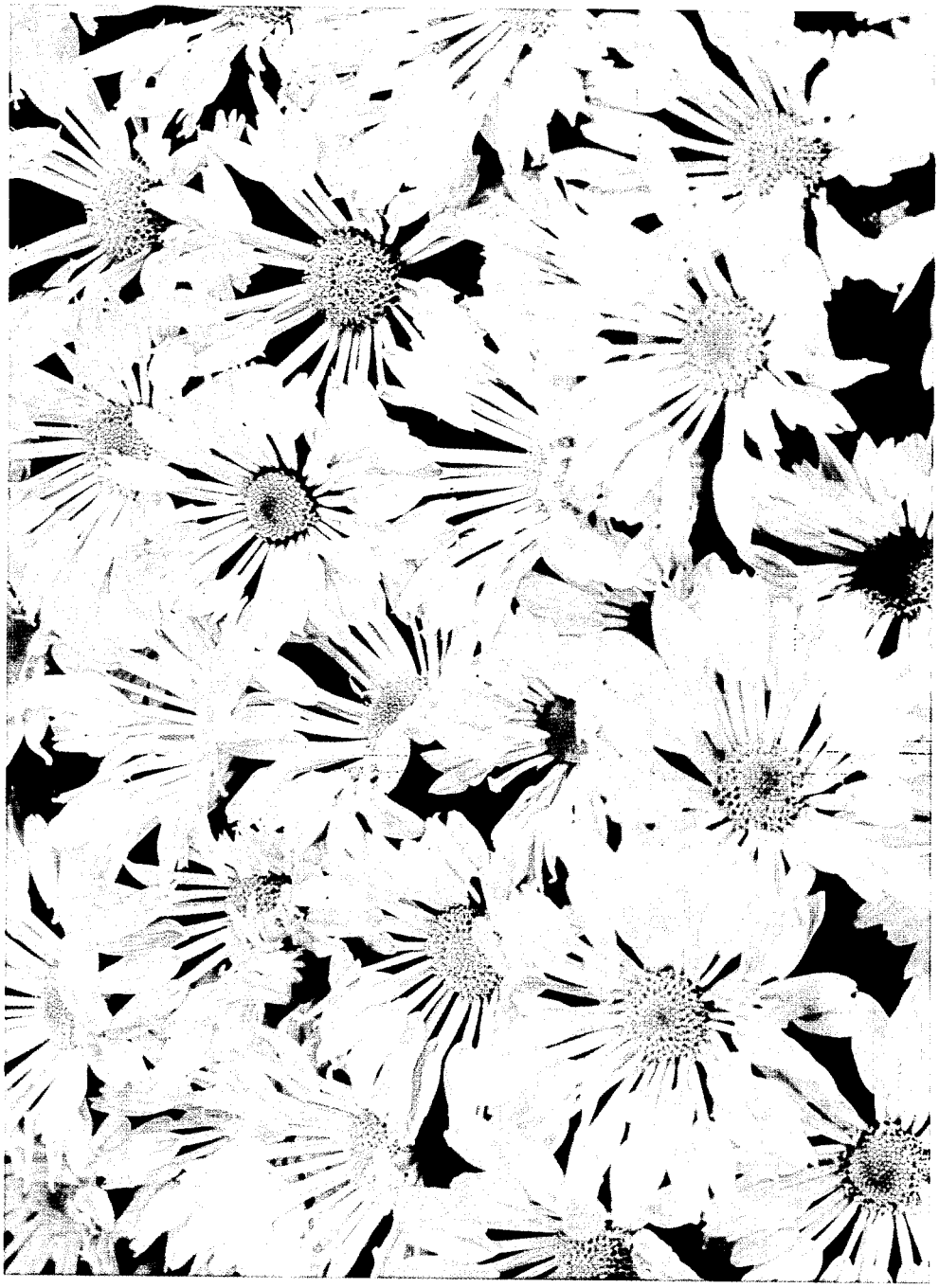

United States Patent Office

Plant Pat. 3,416

Patented Jan. 1, 1974

3,416
CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 22, 1971, Ser. No. 191,893
Int. Cl. A01h *5/00*
U.S. Cl. Plt.—74 1 Claim

The present invention comprises a new and distinct cultivar of daisy form chrysanthemum plant which is a sport of the unpatented cultivar known commercially in the United States as Illini Spinwheel.

The new cultivar is similar in many respects to the parent cultivar Illini Spinwheel, having the same characteristics as Illini Spinwheel of:

(1) Plant habit.
(2) Flower size and unusual flower form.
(3) Period of value.
(4) Flowering response.

The new cultivar is distinguished from Illini Spinwheel by the following unique characteristics when grown under comparable conditions:

Our new cultivar when grown in the vicinity of Barberton, Ohio, has a response period of approximately 8–9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from mid-March through December; coastal California, January through December; and in Florida, November through December, and March through May.

The accompanying photographic drawing shows the unique characteristics of our new cultivar, the color being as nearly true as possible with color illustrations of this type. In the comparison photograph, the new cultivar appears on the left (when looking from the right side of the drawing), and the parent cultivar Illini Spinwheel on the right.

In the following description, color references are made to the Munsell Color Book, 1963 Edition, and color comparisons are made with the cultivar Illini Spinwheel.

Botanical classification: *Chrysanthemum morifolium*

| | Yellow Spinwheel | Illini Spinwheel |
|---|---|---|
| Bloom: | | |
| Size | 1¾″. | |
| Fully expanded | 2¼″. | |
| Borne | Clusters on elongated pedicels. | |
| Stems | Strong | |
| Form | Spooned daisy | |
| Permanence | 10–12 days | |
| Color (Munsell): | | |
| Center of flower | Yellow green, 2.5GY6/10 | Green, 5GY6/6. |
| Base of petals | Yellow green, 2.5GY7/10 | Yellow green, 2.5GY8/10. |
| Inside of petals | Yellow, 7.5Y8.5/12 to light yellow, 10Y9/6 | Ivory, 10Y9/2 to pink, 5R5/8; |
| Reverse of petals | Light yellow, 10Y9/6 | Ivory, 10Y9/1. |
| Tonality from a distance | Yellow | White. |
| Discoloration | Light yellow, 10Y9/6 | Pink, 5R5/8. |
| Petals: | | |
| Texture | Smooth | |
| Appearance and form | Tubular, flaring to spoon at tip, tapering to a blunt multi-notched point. | |
| Arrangement | Composite, whorled on a single receptacle | |
| Persistence | Resist shatter | |
| Fragrance | Typical chrysanthemum | |
| Reproductive organs: | | |
| Stamen, anthers | 150–180 | |
| Pollen | Abundant | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Spreading | |
| Height | Approximately 11″–13″ when timed with 9 week medium to tall treatment as defined in the timetables of Yoder Brothers, Inc., Barberton, Ohio, for the various seasons. | |
| Spread | Approximately 8″ as a pinched plant when timed with 9 week medium to tall treatment as outlined in the Yoder timetables for the various seasons. | |
| Foliage: | | |
| Top side | Dark green, 7.5GY3/4 | |
| Size | 6½″ long, 3¾″ wide | |
| Quantity | Numerous | |
| Shape | Spatulate lobed | |
| Texture | Coarse | |
| Ribs and veins | Prominent | |
| Edge | Deeply indented | |
| Serration | Deeply serrated | |
| Under side | Light green, 7.5GY5/4 | |
| Stipules | Rudimentary | |

(1) Its light yellow flower color.

(2) A sharper, more uniform response particularly in early spring (mid-March through April), and in very late fall (mid-November through December).

(3) An earlier response ranging from one to three days. It is approximately one day May through mid-November, and up to three days earlier mid-March through April, and mid-November through December.

The new cultivar was selected from a flowering block of the parent cultivar in Barberton, Ohio, and when asexually reproduced by cuttings by Yoder Brothers, Inc., at Barberton, Ohio, has been found to retain its distinctive characteristics through successive propagations.

We claim:

1. A new and distinct cultivar of chrysanthemum characterized particularly as to its uniqueness when compared to the parent cultivar Illini Spinwheel by its light yellow flower color, its sharper, more uniform response, particularly in the early spring period of mid-March through April and the very late fall period from mid-November through December, and by its earlier response, ranging from one day in May through mid-November and up to three days earlier in the periods of mid-March through April and mid-November through December.

No references cited.

ROBERT E. BAGWILL, Primary Examiner